US006268539B1

(12) United States Patent
Sen-Huang et al.

(10) Patent No.: US 6,268,539 B1
(45) Date of Patent: Jul. 31, 2001

(54) MANUFACTURING METHOD OF NEOPENTYL GLYCOL

(75) Inventors: Hsu Sen-Huang; Tsai Chia-Ruey; Chuang Jung-Jen, all of Taipei (TW)

(73) Assignee: Nan Ya Plastics Corporation, Taipei (TW)

( * ) Notice: Subject to any disclaimer, the term of this patent is extended or adjusted under 35 U.S.C. 154(b) by 0 days.

(21) Appl. No.: 09/414,725

(22) Filed: Oct. 7, 1999

(51) Int. Cl.$^7$ ................................................. C07C 29/141
(52) U.S. Cl. ............................................ 568/853; 568/854
(58) Field of Search ..................................... 568/853, 854

Primary Examiner—Peter O'Sullivan
(74) Attorney, Agent, or Firm—Bacon & Thomas, PLLC

(57) ABSTRACT

Method and apparatus for producing neopentyl glycol which comprises hydrogenating hydroxypivaldehyde in a reactor provided with a self-aspirator agitator device in the presence of a hydrogenation catalyst. The method has high yield of neopentyl glycol, and does not have to be carried out under high pressure as do certain prior art methods.

11 Claims, 1 Drawing Sheet

MANUFACTURING METHOD OF NEOPENTYL GLYCOL

FIELD OF THE INVENTION

Figure 1:
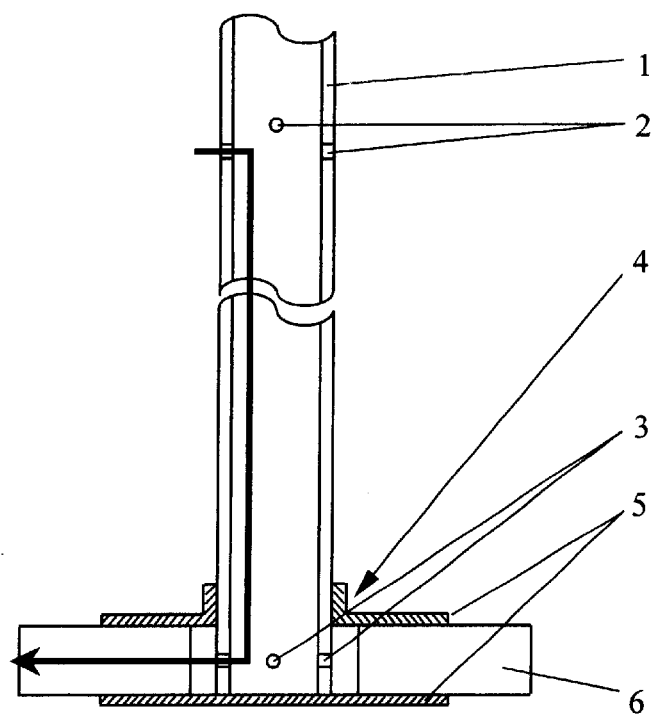

The invention relates to a method for producing neopentyl glycol. More particularly, the invention relates to a method for producing neopentyl glycol using a reactor provided with a self-aspirator device in the presence of a hydrogenation catalyst by hydrogenation of hydroxypivaldehyde.

BACKGROUND OF THE INVENTION

Neopentyl glycol (hereinafter as "NPG") is an important starting material for the preparation of various useful products such as synthetic resins, lubricants, surface coatings and plastics. NPG has commonly been produced by effecting an aldol condensation of isobutyraldehyde and formaldehyde, followed by the hydrogenation of the condensation product, hydroxypivaldehyde, such as those described in U.S. Pat. No. 2,400,724, U.S. Pat. No. 2,865,819 and U.S. Pat. No. 3,939,216. The type of aldol catalyst used with condensation reaction have been a base catalyst, such as alkali metal-containing catalyst, alkaline earth metal-containing catalyst and tertiary amines; the type of catalyst used with hydrogenation have been a heterogeneous catalyst, such as copper/chromium oxide, Pt-Ru-W and Raney nickel. The hydrogenation of the condensation product, hydroxypivaldehyde, has commonly been carried out by the gas sparged reactor, such as those described in U.S. Pat. No. 4,855,515. However, owing to the low efficiency of gas-liquid contact in the gas sparged reactor, low yield of NPG is obtained, unless it is necessary to conduct the hydrogenation under high pressures. These caused constraints on the process and equipment to be used and considerable problems, in particular in industry plants, where one must ensure high standards of safety and reliability, and high yield of NPG.

It is thus desirable to have a method which have high efficiency of gas-liquid contact for high yield of NPG, and without the need to conduct the reaction at high pressures.

SUMMARY OF THE INVENTION

It has now been discovered that high yields of necpentyl glycol can be obtained in the hydrogenation of hydroxypivaldehyde crude product without the need of high pressures in the hydrogenation, on the condition that the hydrogenation is conducted in a reactor provided with a self-aspirator agitator using a hydrogenation catalyst. Use of the reactor provided with a self-aspirator agitator device design in this hydrogenation reaction has been found to achieve the desired high yields because it has high efficiency of gas-liquid contact in the reactor during the hydrogenation. This high efficiency of gas-liquid contact maintains the hydrogen in the liquid at very high concentrations thereby maximize the activity of hydrogenation catalysts, and allowing for greater yield of NPG from the hydroxypivaldehyde. For this reason, and unlike prior art methods, the method of the invention allows for the production of high yields of NPG without the necessity of conducting the hydrogenation under high pressures.

DETAILED DESCRIPTION OF THE INVENTION

The aldol condensation reaction is commonly carried out in an aldol reactor which is fed isobutyraldehyde, formaldehyde and a base catalyst. It is desirable to react these components in an aqueous solution with the formaldehyde being preferably introduced into the reactor as a 20 to 50 weight percent aqueous solution. The molar ratio of isobutyraldehyde to formaldehyde should be maintained at from 1.1:1 to 1.4:1. The amount of base catalyst needed is variable, but the total amount of base catalyst included generally in the range from about 0.2 to about 3.0 weight percent of the reaction mixture. The aldol condensation reaction is carried out at temperatures from about 70° C. to about 100° C., and a 10–25 psig nitrogen pressure is applied to ensure that the reactants will be kept in liquid form. A residence time of anywhere from about an hour to about three hour is usually sufficient to effect the condensation reaction. The hydroxypivaldehyde produced in this reactor will contain other materials such as some unreacted isobutyraldehyde as well as some base catalyst and base-containing residues. The hydroxypivaldehyde product of the aldol condensation reaction will be mostly isobutyraldehyde (3 wt %–7 wt %), hydroxypivaldehyde (about 43 wt %–70 wt %), water (about 20 wt %–51 wt %), catalyst (0.2 wt %–3 wt %), NPG (0.2 wt %–1 wt %), methanol (0.5 wt %–3 wt %) and impurities (0.8 wt %–2.0 wt %).

The hydroxypivaldehyde product so obtained is then introduced directly or the unreacted reactants are recovered by distillation to get crude hydroxypivaldehyde, or further add a solvent to the crude hydroxypivaldehyde, then introduced into a reactor provided with a self-aspirator agitator device. The solvent is selected from the group consisting of (i) water (ii) at least one alcohol selected from the group consisting of methanol, ethanol, propanol, butanol, hexanol, octanol and neopentyl glycol and (iii) mixture of water and at least one alcohol selected from the group consisting of methanol, ethanol, propanol, butanol, hexanol, octanol and neopentyl glycol.

By a "reactor provided with a self-aspirator agitator device" as used in the invention is meant a reactor which includes a gas-tight vessel which can withstand pressure, a rotatory agitator device providing for stirring and promoting the contact between the gas and the liquid in the vessel.

According to the invention, the device used for stirring and promoting the efficiency of gas-liquid contact is of the self-aspirator type; it can include a rotatory hollow shaft with suction openings for the gas in its upper part and venting openings with a propeller in its lower part. This agitator device can further be provided with additional circulators and baffles. In addition, the gas-tight vessel can further be provided with coils or plates of the heat exchanger.

The shape of the vessel is, for example, cylindrical, with the concave bottom being elliptical, hemispherical, or the like. A conical bottom can also be used. The upper part can be formed with a cover which is either fastened with a flarge or welded, and of which the shape is not essential for the present invention. To achieve an adequate stirring of the liquid and an effective suction of the gas, it is advantageous to maintain a ratio of the length of the cylinder to its diameter between 0.4 and 3.0. To enable the introduction of the gas into the reactor and to ensure the stirring of the liquid, the apparatus includes an agitator device of the self-aspirator type, which will be described in detail further by the accompanying drawings illustrating schematically and by way of only one embodiment example of the apparatus for the hydrogenation of the hydroxypivaldehyde.

Figure 2:
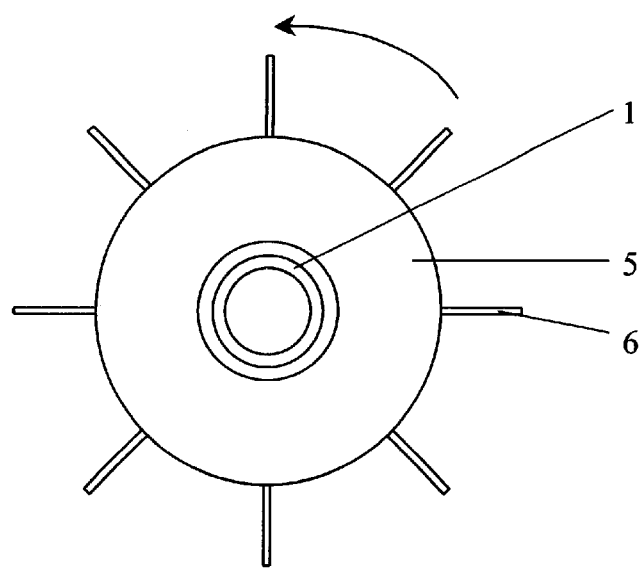

FIGS. 1 and 2 are partial views illustrating a self-aspirator agitator device which can be used in the apparatus according to the invention.

The self-aspirator agitator device includes a hollow, shaft 1 rotatably driven by a motor and exhibiting suction openings 2 for the gas in its upper part and venting openings 3 with a propeller 4 located in the middle of the vessel. This propeller 4 is fixed by upper, lower disc 5. According to a preferred embodiment, the blades 6 of the propeller 4 are of a plate, a concave or a bent shape, to provide an enhanced centrifugation of the liquid.

To improve the circulation of the liquid in the vessel and to prevent too fast a coalescence of the bubbles of gas in the liquid, the agitator device can further be provided with additional circulators and baffles. The driving system of the agitator device is selected in such a manner as to ensure gas-tightness of the apparatus, and eliminate any risks of leakage into the environment, for example it can be a magnetic driving system; other devices using conventional systems including mechanical safety seals can also be used.

It is preferred that the hydrogenation reactor of crude hydroxypivaldehyde be maintained at a temperature of from 70° C. to 120° C., and that a hydrogen pressure of from about 80 to 1800 pounds per square inch gauge (psig) be applied. The amount of hydrogenation catalyst employed generally varies from about 0.2 to about 15 weight percent of the hydroxypivaldehyde. It is particularly preferred that the hydrogenation catalyst be about 1 to 10 weight percent of the hydroxypivaldehyde. The hydrogenation reaction residence time should be in a range of about 1 to 6 hours.

The crude NPG liquid product will contain 42–80 weight percent NPG, 16–54 weight percent solvent, and minor amounts of isobutanol, methanol and impurities.

This crude NPG product can then be treated with sodium hydroxide to saponify any ester by-products. Sodium hydroxide should be introduced in amount equal to about 1% weight of NPG product at a temperature of about 90° C. The NPG stream is then distilled to remove low boiling point isobutanol and methanol etc.. The NPG/solvent mixture can then be further distilled from sodium containing salts by flash distillation. If necessary, further distillation to remove remaining solvent can be undertaker. Optionally a 98% to 100% yield of conversion of hydroxypivaldehyde into NPG is obtained. The NPG will contain only trace amounts of impurities.

According to the invention, reaction vessel having, a hollow shaft stirring can be used in the hydrogenation of hydroxypivaldehyde to elevate the contact efficiency between hydrogen and reactant liquid in the reaction vessel and reduce the operating pressure, this also elevate the yield of conversion of hydroxypivaldehyde into NPG.

While the specification concludes with claims particularly pointing out and distinctly claiming the subject matter of the invention, it is believed the invention will be better understood from the following description taken in connection with the accompanying drawing.

EXAMPLE 600 g of condensation product that resulted from reacting isobutyraldehyde and formaldehyde solution in the presence of triethylamine is distilled to remove the isobutyraldehyde and triethylamine. The results of distillation is 560 g of crude hydroxypivaldehyde which contain 1.4 weight percent isobutyraldehyde, 71 weight percent hydroxypivaldehyde, 21 weight percent $H_2O$, 0.2 weight percent triethylamine, 1.3 weight percent NPG, 0.1 weight percent methanol and 5 weight percent impurities. This crude hydroxypivaldehyde is charged to a 1 liter hydrogenation reactor provided with a self-aspirator agitator device, then 12 g of molybdenum promoted Raney nickel is added and the reactor is purged by hydrogen. The reactor is pressurized to 440 psig by hydrogen, and kept in this pressure. Then the reactor is operated at 100° C. under 500 rpm stirring of agitator for 2 hours. The yield of conversion of hydroxypivaldehyde into NPG is 99.8%.

Comparative Example 1

All is the same as example 1 but self-aspirator agitator device is replaced by a unself-aspirator agitator device with a gas sparger. The yield of conversion of hydroxypivaldehyde into NPG is 41.4%.

Comparative Example 2

All is the same as example 2 but 440 psig is replaced by 880 psig of hydrogen pressure. The yield of conversion of hydroxypivaldehyde into NPG is 71.5%.

What is claimed is:

1. A method for producing neopentyl glycol which comprises hydrogenating hydroxypivaldehyde dissolved in the solvent in a reactor provided with a self-aspirator agitator device in the presence of a hydrogenation catalyst at a temperature of 70° to 120° C. and a pressure of 80 to 1800 psig maintained by introducing hydrogen.

2. A method according to claim 1 wherein the hydroxypivaldehyde is an aldol condensation reaction crude product which is obtained by reacting isobutyraldehyde with formaldehyde in the presence of a base catalyst with or without removing the unwanted components.

3. A method according to claim 2 wherein the solvent is selected from the group consisting of (i) water (ii) at least one alcohol selected from the group consisting of methanol, ethanol, propanol, butanol, hexanol, octanol, and neopentyl glycol and (iii) mixture of water and at least one alcohol selected from the group consisting of methanol, ethanol, propanol, butanol, hexanol, octanol, and neopentyl glycol.

4. A method according to claim 1 wherein the hydrogenation is carried out in the batch or semi-batch or continuous operation.

5. A method according to claim 1 wherein the hydrogenation is effected at a temperature of 80° to 110° C. and a pressure of 140 to 1400 psig.

6. A method according to claim 1 wherein the amount of hydrogenation catalyst employed is 0.2 to 15 weight percent of the hydroxypivaldehyde.

7. A method according to claim 6 wherein the amount of hydrogenation catalyst employed is 1 to 10 weight percent of the hydroxypivaldehyde.

8. A method according to claim 1 wherein the hydioxypivaldehyde is in a solution in a concentration of 5 to 85 weight percent.

9. A method according to claim 7 wherein the hydroxypivaldehyde is in a solution in a concentration of 10 to 80 weight percent.

10. A method according to claim 1 wherein the hydrogenation reaction is carried out for about 1 to 6 hours.

11. A method according to claim 1 wherein the hydrogenation catalyst can be used in the range from 1 to 10 weight percent of the hydroxypivaldehyde.

\* \* \* \* \*